US012740695B1

(12) United States Patent
Li et al.

(10) Patent No.: US 12,740,695 B1
(45) Date of Patent: Sep. 22, 2026

(54) VISUAL TWEEZERS AND DRIVING MECHANISM THEREOF

(71) Applicant: Shenzhen Sulang Technology Co., Ltd., Shenzhen City (CN)

(72) Inventors: Zhengzhong Li, Shaoyang City (CN); Wenming Li, Shaoyang City (CN)

(73) Assignee: Shenzhen Sulang Technology Co., Ltd., Shenzhen City (CN)

( * ) Notice: Subject to any disclaimer, the term of this patent is extended or adjusted under 35 U.S.C. 154(b) by 0 days.

(21) Appl. No.: 19/396,615

(22) Filed: Nov. 21, 2025

(30) Foreign Application Priority Data

Oct. 16, 2025 (CN) ......................... 202522199708.0

(51) Int. Cl.

| | |
|---|---|
| ***A61B 1/227*** | (2006.01) |
| ***A61B 1/00*** | (2006.01) |
| ***A61B 1/05*** | (2006.01) |
| ***A61F 11/00*** | (2022.01) |

(52) U.S. Cl.
CPC .......... *A61B 1/227* (2013.01); *A61B 1/00133* (2013.01); *A61B 1/05* (2013.01); *A61F 11/006* (2013.01)

(58) Field of Classification Search
CPC ....... A61B 1/227; A61B 1/00133; A61B 1/05; A61B 1/006
See application file for complete search history.

(56) References Cited

U.S. PATENT DOCUMENTS

| | | | | |
|---|---|---|---|---|
| 216,918 | A * | 6/1879 | Wales | B25B 9/02 119/806 |
| 4,318,313 | A * | 3/1982 | Tartaglia | B25B 9/02 294/99.2 |
| 6,202,760 | B1 * | 3/2001 | Lin | B24B 23/022 173/132 |
| 7,625,028 | B2 * | 12/2009 | Cho | B25B 9/02 294/99.2 |
| 11,890,028 | B1 * | 2/2024 | Dai | A61B 1/05 |
| 11,940,445 | B2 * | 3/2024 | Refaai | G01N 33/5304 |
| 12,440,388 | B2 * | 10/2025 | Dai | A61F 11/006 |
| 2024/0306893 | A1 * | 9/2024 | Wang | A61B 1/00105 |

FOREIGN PATENT DOCUMENTS

| | | |
|---|---|---|
| CN | 215651987 U | 1/2022 |
| CN | 217020020 U | 7/2022 |

* cited by examiner

*Primary Examiner* — Eduardo C Robert
*Assistant Examiner* — Holly Joanna Lane

(57) ABSTRACT

Disclosed is a driving mechanism of visual tweezers, which is configured to be mounted on the visual tweezers to drive a tweezer head to clamp or release. The driving mechanism includes a mounting base and a driving assembly. The mounting base is provided with a mounting hole and a driving hole. The driving assembly includes a movable key, a driving member, a reset spring, and a driving tube. The movable key is mounted in the mounting hole. The driving member is disposed in the mounting base and movably abuts against the movable key. One end of the reset spring is mounted on the driving member, and the other end abuts against an inner wall of the mounting base. One end of the driving tube is located outside the mounting base, and the other end extends into the mounting base from the driving hole and is fixed on the driving member.

9 Claims, 7 Drawing Sheets

VISUAL TWEEZERS AND DRIVING MECHANISM THEREOF

CROSS-REFERENCE TO RELATED APPLICATIONS

The application claims priority of Chinese patent application 202522199708.0, filed on Oct. 16, 2025, which is incorporated herein by reference in its entireties.

TECHNICAL FIELD

The present invention relates to the technical field of healthcare, and in particular, to visual tweezers and a driving mechanism thereof.

BACKGROUND

With the continuous development of healthcare devices, visual ear scoops have been gradually applied to daily ear canal cleaning. Existing visual ear scoops typically include a scoop portion, a handle portion, a camera disposed at a connection position of the scoop portion and the handle portion, and a wireless transmission module configured to transmit an image to an external visual terminal. A user observes an internal condition of an ear canal through a terminal screen, assistance in determining the position of earwax is provided, and the scoop portion is operated to perform cleaning.

However, during actual use, when earwax having a large size or a hard texture is encountered, complete removal is difficult to achieve through the scoop portion alone, and replacement with a tweezer head is required to operate. However, a main body of the ear scoop has a large volume and occupies a large amount of space in a narrow ear canal, a tweezer head has severely limited clamping operation space, and the handle portion is difficult to apply force flexibly, thereby causing an inconvenient operation after replacement and poor cleaning effectiveness.

SUMMARY

A primary objective of the present invention is to provide a driving mechanism of visual tweezers, which aims to improve the practicality of the visual tweezers.

To achieve the above objective, the driving mechanism of visual tweezers proposed by the present invention is configured to be mounted on the visual tweezers to drive a tweezer head on the visual tweezers to clamp or release, and includes:

- a mounting base, where the mounting base is provided with a mounting hole and a driving hole; and
- a driving assembly, where the driving assembly includes a movable key, a driving member, a reset spring, and a driving tube, the movable key is mounted in the mounting hole, the driving member is disposed in the mounting base and movably abuts against the movable key, one end of the reset spring is mounted on the driving member, the other end of the reset spring abuts against an inner wall of the mounting base, one end of the driving tube is located outside the mounting base, and the other end of the driving tube extends into the mounting base from the driving hole and is fixed on the driving member.

Preferably, the movable key is provided with an inclined first driving surface, the driving member is provided with a second driving surface cooperating with the first driving surface, and the first driving surface movably abuts against the second driving surface.

Preferably, two mounting holes are provided, the two mounting holes are arranged opposite to each other on the mounting base, and a number of the movable keys corresponds to a number of the mounting holes.

Preferably, the two movable keys are connected through a connecting member.

Preferably, the driving member is provided with a first mounting groove, and the driving tube is inserted into the first mounting groove.

Preferably, the driving member is provided with a second mounting groove, and one end of the reset spring is mounted in the second mounting groove.

Preferably, the mounting base includes a first mounting base and a second mounting base, the first mounting base is mounted on the second mounting base to form a mounting space, and the driving member is disposed in the mounting space and movably abuts against the second mounting base.

Preferably, the mounting base is provided with a third mounting groove adapted to a visual tweezer body, one end of the visual tweezer body is fixed in the third mounting groove, and a limiting hole corresponding to the driving hole is provided in a groove wall of the third mounting groove.

The present invention further provides visual tweezers, which include a tweezer body and a driving mechanism of the visual tweezers; the tweezer body includes a mounting tube and a tweezer head detachably mounted on the mounting tube, the mounting tube is inserted into the driving tube, and two sides of the tweezer head abut against a tube opening of the driving tube.

Preferably, the tweezer body further includes a camera, and the camera is disposed in the mounting tube and arranged near the tweezer head.

The driving mechanism of visual tweezers provided by the technical solution of the present invention is configured to be mounted on the visual tweezers to drive a tweezer head to clamp or release. The driving mechanism includes: a mounting base, where the mounting base is provided with a mounting hole and a driving hole; and a driving assembly, where the driving assembly includes a movable key, a driving member, a reset spring, and a driving tube, the movable key is mounted in the mounting hole, the driving member is disposed in the mounting base and movably abuts against the movable key, one end of the reset spring is mounted on the driving member, the other end of the reset spring abuts against an inner wall of the mounting base, one end of the driving tube is located outside the mounting base, and the other end of the driving tube extends into the mounting base from the driving hole and is fixed on the driving member. Through the above structure, when a pressing force is applied to the movable key, the movable key drives the driving member to move, thereby driving the driving tube to move and causing the tweezer head to perform a clamping action; and when the movable key is released, the reset spring restores to an original state and pushes the driving member back to an initial position, and the driving tube simultaneously returns to a reset position, thereby restoring the tweezer head to a releasing state. This effectively improves the practicality of the visual tweezers.

BRIEF DESCRIPTION OF THE DRAWINGS

To more clearly illustrate the technical solutions in the embodiments of the present invention or in the prior art, the drawings required to be used in the description of the embodiments or the prior art are briefly introduced below. It is obvious that the drawings in the description below are only some embodiments of the present invention, and those of ordinary skill in the art can obtain other drawings according to structures illustrated in these drawings without creative efforts.

DESCRIPTIONS OF REFERENCE NUMERALS

Figure 1:
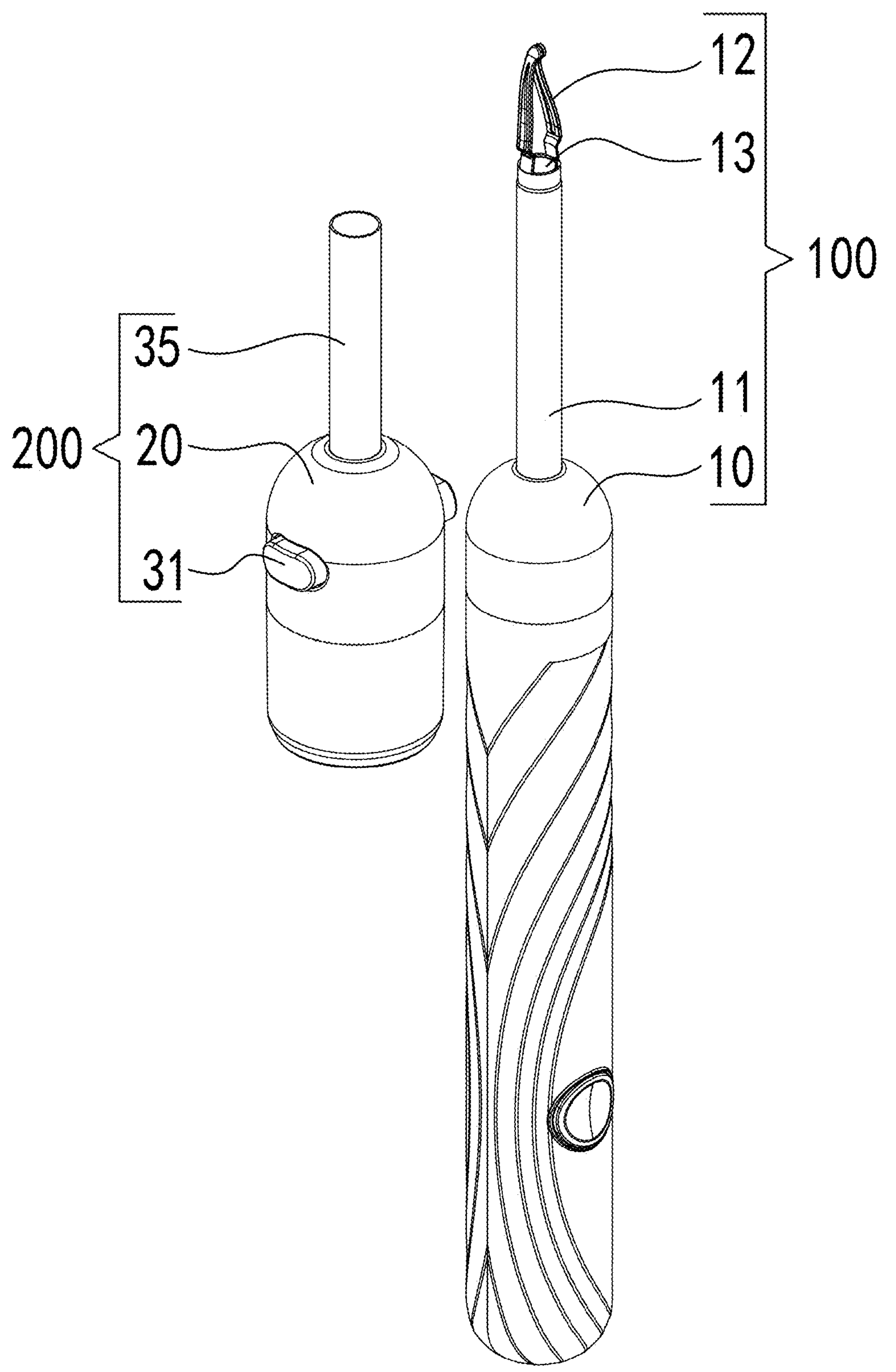
FIG. 1 is a schematic diagram of an exploded structure of visual tweezers according to the present invention from one angle.

100. visual tweezers; 10. tweezer body; 11. mounting tube; 12. tweezer head; 13. camera; 14. control board; 200. driving mechanism; 20. mounting base; 21. mounting hole; 22. driving hole; 23. first mounting base; 24. second mounting base; 25. third mounting groove; 26. limiting hole; 30. driving assembly; 31. movable key; 311. first driving surface; 32. driving member; 321. second driving surface; 322. first mounting groove; 323. second mounting groove; 33. connecting member; 34. reset spring; and 35. driving tube.

The realization of the objectives, the functional features, and the advantages of the present invention will be further explained in conjunction with the embodiments and with reference to the drawings.

DETAILED DESCRIPTION OF THE EMBODIMENTS

The technical solutions in the embodiments of the present invention will be clearly and completely described below with reference to the drawings in the embodiments of the present invention. It is apparent that the described embodiments are only some, but not all, embodiments of the present invention. Based on the embodiments of the present invention, all other embodiments obtained by those of ordinary skill in the art without creative efforts fall within the protection scope of the present invention.

It should be noted that, if directional indications (such as upper, lower, left, right, front and rear) are involved in the embodiments of the present invention, the directional indications are only used to explain the relative positional relationships, the motion situations and the like between individual components under a certain pose (as shown in the drawings), and if the certain pose is changed, the directional indications are changed accordingly.

In addition, if there are descriptions relating to "first", "second" and the like in the embodiments of the present invention, the descriptions of "first", "second" and the like are for descriptive purposes only and are not to be construed as indicating or implying relative importance thereof or implicitly indicating the quantities of the indicated technical features. Thus, a feature defined by "first" or "second" may explicitly or implicitly include at least one such feature. In addition, "and/or" appearing herein is meant to include three parallel solutions, and taking "A and/or B" as an example, it includes solution A, or solution B, or both solution A and solution B. In addition, the technical solutions among various embodiments may be combined with each other; however, this combination must be based on that it can be implemented by those of ordinary skill in the art. When the combination of the technical solutions is contradictory or cannot be implemented, such a combination of the technical solutions should not be considered to exist, and is not within the protection scope of the present invention.

The present invention provides a driving mechanism 200 of visual tweezers 100, which is configured to be mounted on the visual tweezers 100 to drive a tweezer head 12 on the visual tweezers 100 to clamp or release.

In embodiments of the present invention, as shown in FIGS. 1 to 5, the driving mechanism 200 of the visual tweezers 100 includes a mounting base 20 and a driving assembly 30. The mounting base 20 is provided with a mounting hole 21 and a driving hole 22, the mounting hole 21 is configured to mount a movable key 31, and the driving hole 22 is configured for a driving tube 35 to extend through. The driving assembly 30 includes a movable key 31, a driving member 32, a reset spring 34, and a driving tube 35. The movable key 31 is mounted in the mounting hole 21. The driving member 32 is disposed in the mounting base 20 and movably abuts against the movable key 31. One end of the reset spring 34 is mounted on the driving member 32, and the other end of the reset spring 34 abuts against an inner wall of the mounting base 20. One end of the driving tube 35 is located outside the mounting base 20, and the other end of the driving tube 35 extends from the driving hole 22 and is fixed on the driving member 32. During use, a user presses the movable key 31 to drive the driving member 32 to move inward, the driving tube 35 moves forward accordingly to press the tweezer head 12, thereby clamping a target. When the movable key 31 is released, the reset spring 34 elastically rebounds to drive the driving member 32 and the driving tube 35 to return to the initial positions, and the tweezer head 12 is correspondingly released, thereby achieving a switch between clamping and releasing. This structure allows simple operation and effectively improves the flexibility and reliability of the tweezers.

Further, as shown in FIGS. 4 to 8, in another embodiment, the movable key 31 is provided with an inclined first driving surface 311, the driving member 32 is provided with a second driving surface 321 cooperating with the first driving surface 311, and the two surfaces movably abut against each other. Through the inclined surface cooperation, when the user presses the movable key 31, the vertical pressing force is converted into an axial driving force of the driving member 32 by the inclined surface, thereby driving the driving tube 35 to move forward smoothly and press the tweezer head 12. This inclined surface force-transmission structure avoids jamming during linear pushing, distributes force evenly on the driving member 32, increases transmission efficiency, and ensures that the opening and closing process of the tweezer head 12 is smooth.

In a further embodiment, two mounting holes 21 are provided and arranged opposite each other on two sides of the mounting base 20, and two movable keys 31 are provided correspondingly. The dual-key design allows a user to apply force simultaneously on two sides according to an operating habit, thereby distributing force more evenly on the driving member 32 and ensuring stable movement of the driving tube 35. This not only improves operational convenience, but also enhances the overall applicability of the structure.

Further, the two movable keys 31 are connected through a connecting member 33. When the user presses either one of the keys, the other key moves synchronously, thereby maintaining balanced force on the driving member 32 at all times, preventing friction or jamming caused by tilting, and ensuring smoother movement of the driving tube 35. This design improves clamping accuracy and reliability of the tweezer head 12.

Figure 2:
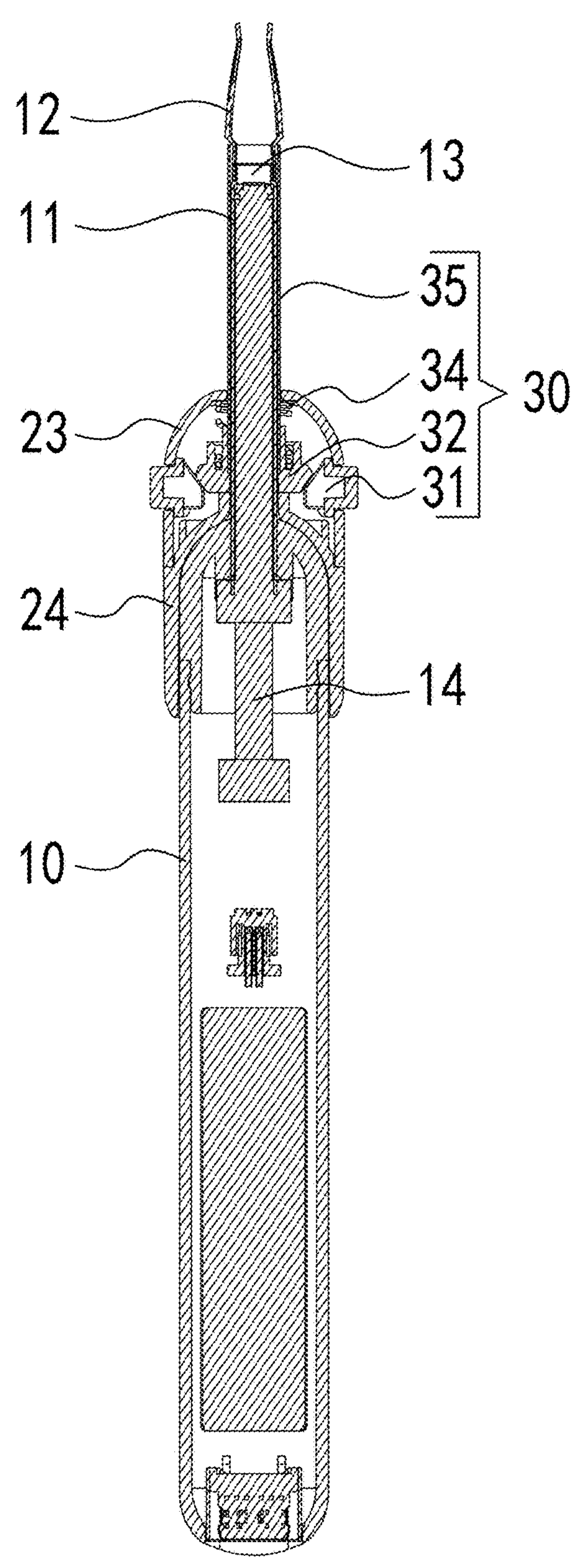
FIG. 2 is a schematic diagram of a cross-sectional structure of visual tweezers according to the present invention in a clamped state.
Figure 7:
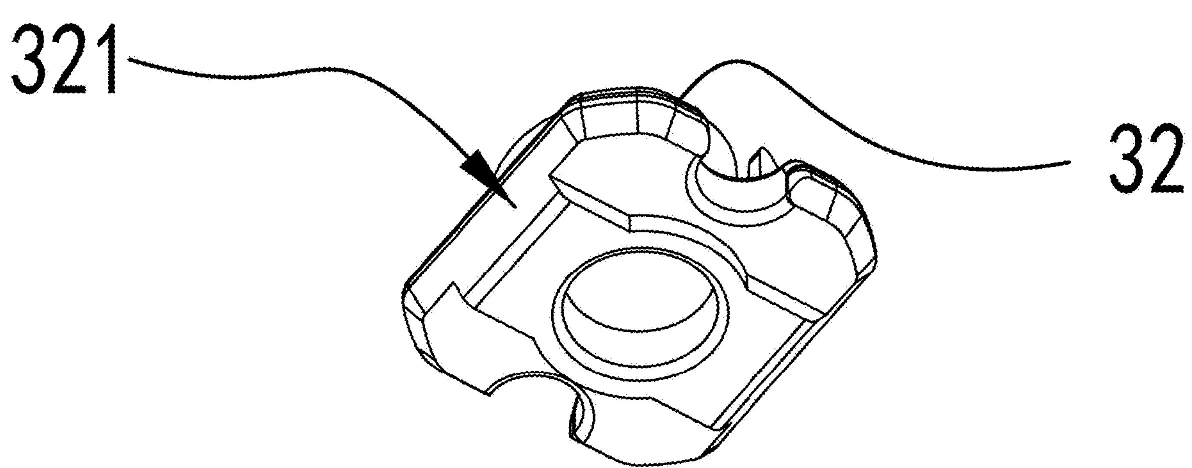
FIG. 7 is a schematic diagram of a structure of a driving member from another angle.
Figure 8:
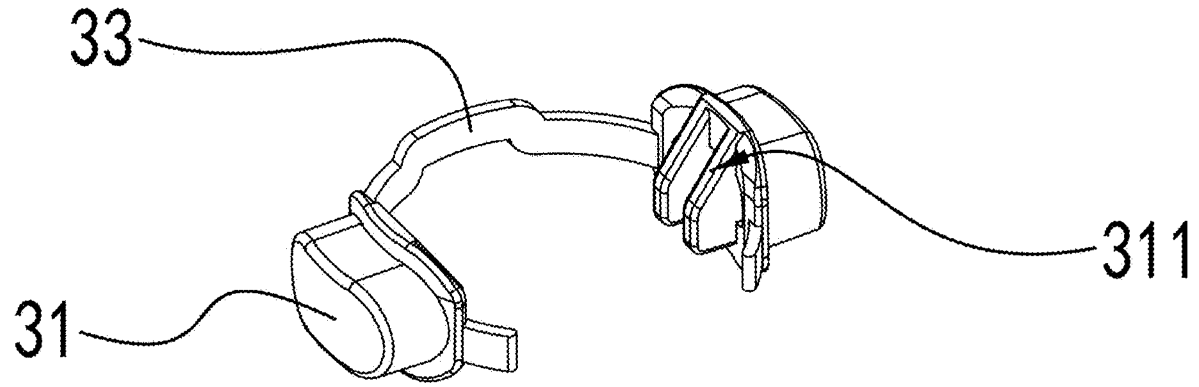
FIG. 8 is a schematic diagram of a structure of a movable key from one angle.

Further, as shown in FIGS. 2 and 7, in another embodiment, the driving member 32 is provided with a first mounting groove 322, and the driving tube 35 is inserted into the first mounting groove 322 and fixedly connected thereto. Through the limiting function of the first mounting groove 322, the cooperation between the driving tube 35 and the driving member 32 is more stable, which prevents loosening or misalignment of the driving tube 35 during use. The driving tube 35 is driven by the driving member 32 to move linearly along the axial direction, thereby ensuring the accuracy of the clamping and releasing actions of the tweezer head 12.

Figure 6:
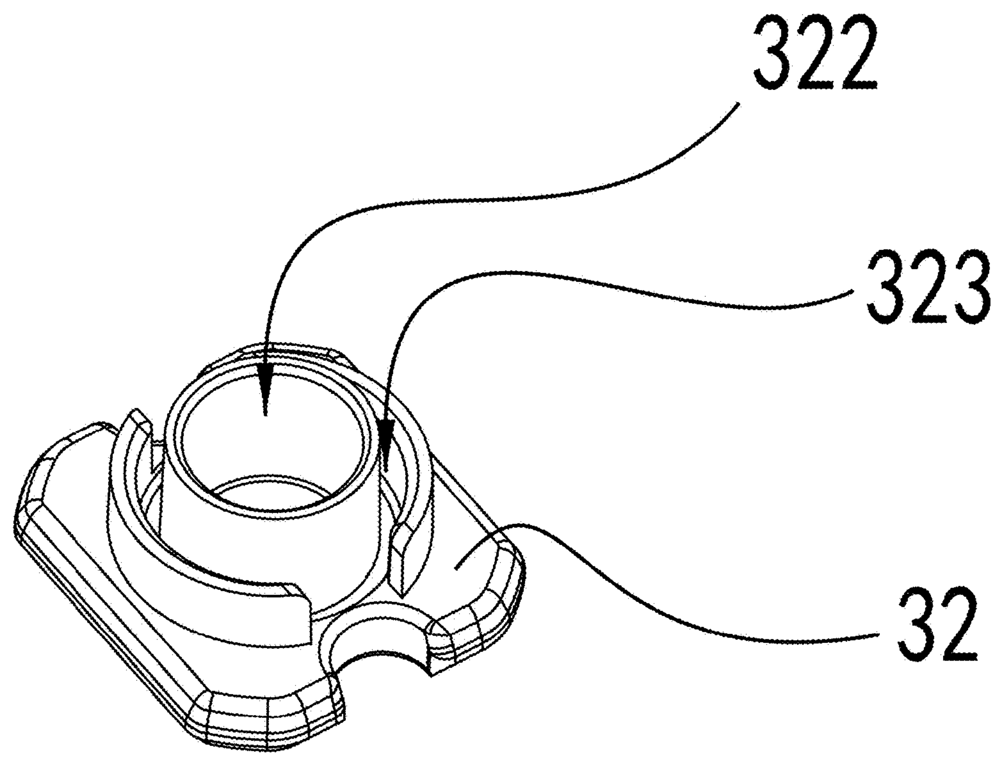
FIG. 6 is a schematic diagram of a structure of a driving member from one angle.

Further, as shown in FIG. 6, in another embodiment, the driving member 32 is provided with a second mounting groove 323, and one end of the reset spring 34 is fixed in the second mounting groove 323. This structure provides a precise positioning space for the reset spring 34, which prevents displacement or detachment during movement, and ensures that compression and rebound of the reset spring 34 occur along a predetermined direction. As a result, the reset direction of the driving member 32 is accurate, the driving tube 35 moves smoothly, and the clamping and releasing of the tweezer head 12 are performed efficiently and stably.

Figure 4:
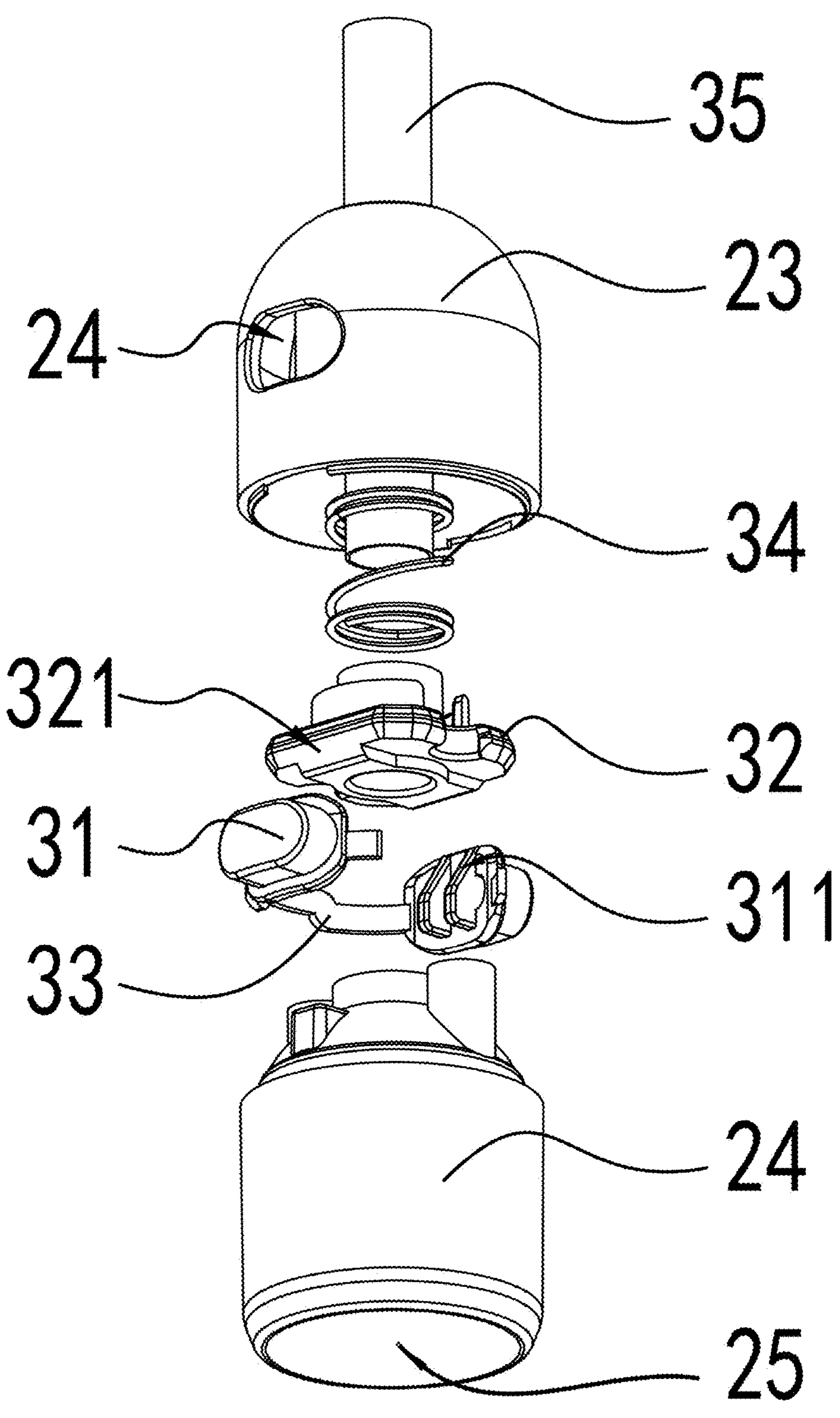
FIG. 4 is a schematic diagram of an exploded structure of a driving mechanism of visual tweezers according to the present invention from one angle.
Figure 5:
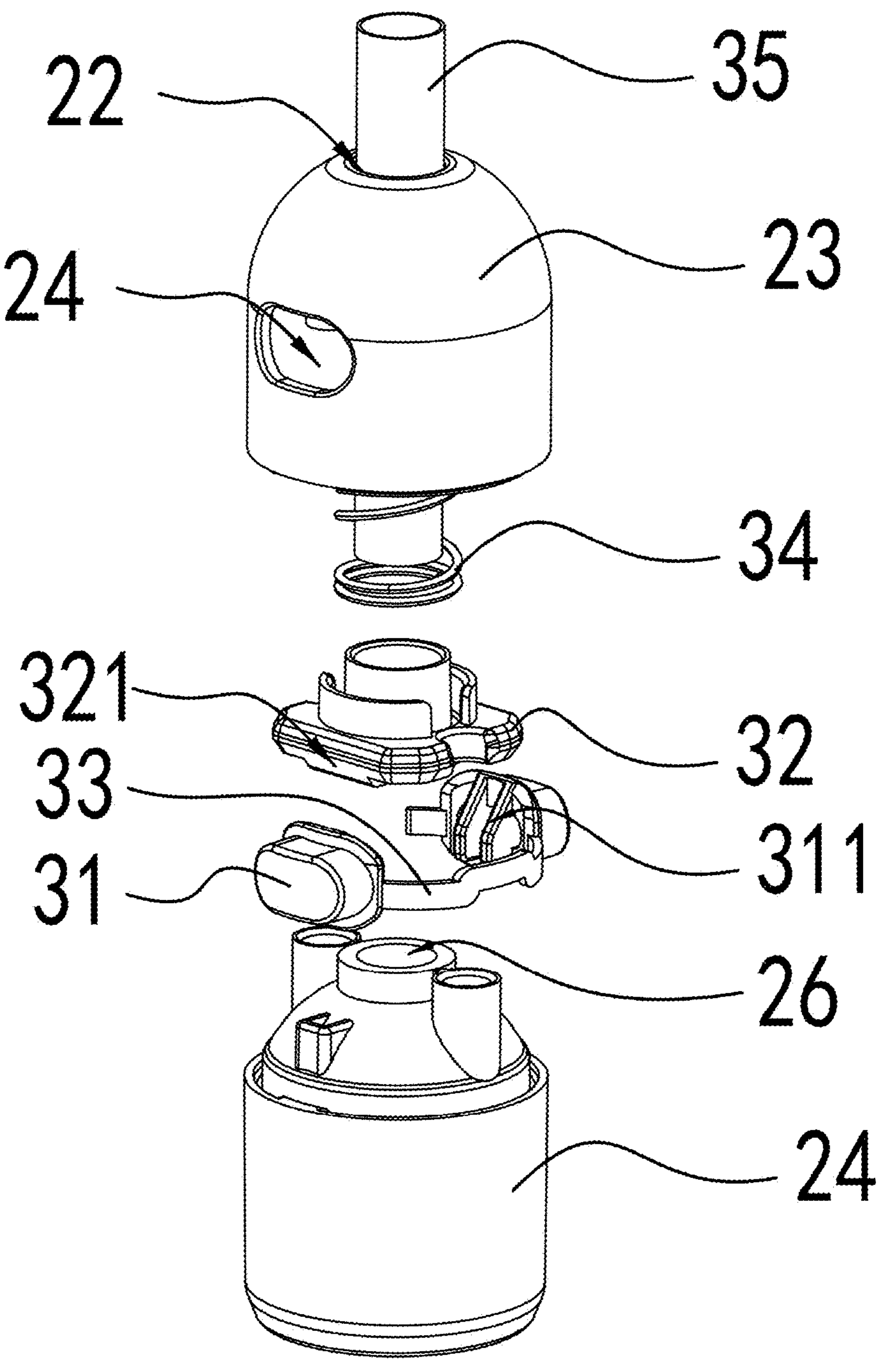
FIG. 5 is a schematic diagram of an exploded structure of a driving mechanism of visual tweezers according to the present invention from another angle.

Further, as shown in FIGS. 4 and 5, in another embodiment, the mounting base 20 includes a first mounting base 23 and a second mounting base 24, the first mounting base 23 is fixed on the second mounting base 24 to form a mounting space, and the driving member 32 is disposed in the mounting space and movably abuts against the second mounting base 24. Through the split-type structure of the mounting base 20, the mounting and maintenance of the driving member 32 are more convenient, and the mounting space constrains the movement trajectory of the driving member 32, ensuring smooth sliding and preventing shaking. This effectively improves the structural strength and durability of the entire driving mechanism 200.

Further, as shown in FIG. 4, in another embodiment, the mounting base 20 is provided with a third mounting groove 25 adapted to a visual tweezer body 10, and one end of the visual tweezer body 10 is fixed in the third mounting groove 25. A limiting hole 26 corresponding to the position of the driving hole 22 is provided in a groove wall of the third mounting groove 25. The limiting hole 26 is configured to define a stroke of the driving tube 35, preventing horizontal movement of the driving tube 35 and thereby avoiding potential injury to a user. Through this design, the tweezer body 10 and the driving mechanism 200 can be securely coupled while ensuring operational safety.

The present invention further provides visual tweezers 100. The visual tweezers 100 include a tweezer body 10 and the driving mechanism 200 of the visual tweezers 100 according to any one of the above embodiments. A detailed structure of the driving mechanism 200 is described with reference to the above embodiments. Since the visual tweezers 100 adopt all of the technical solutions of the above embodiments, the visual tweezers 100 have at least all of the beneficial effects provided by the above embodiments. Details are not described herein. The tweezer body 10 includes a mounting tube 11 and a detachable tweezer head 12. The mounting tube 11 is inserted into the driving tube 35, the tweezer head 12 is mounted at one end of the mounting tube 11, and two sides of the tweezer head 12 abut against a tube opening of the driving tube 35. When the driving tube 35 moves forward, the tube opening presses two sides of the tweezer head 12 to clamp a target. When the driving tube 35 returns, the tweezer head 12 naturally opens and releases the target. Through a sleeved fit between the mounting tube 11 and the driving tube 35 and a detachable connection of the tweezer head 12, stable clamping during operation is achieved, and the replacement of the tweezer head 12 is facilitated, thereby improving the applicability and extensibility of the product.

In addition, a maximum diameter of the tweezer head 12 in the releasing state is greater than a diameter of the driving tube 35. Such dimensional matching enables the tweezer head 12 to naturally open when no driving force is applied, thereby providing a larger clamping range. When the driving tube 35 moves forward, the tube opening forces the tweezer head 12 to gradually close until the target is clamped. Through the structural characteristics of automatic opening and forced clamping, the tweezer head 12 is capable of accommodating foreign objects of different sizes and shapes, thereby improving operational flexibility and reliability.

Figure 3:
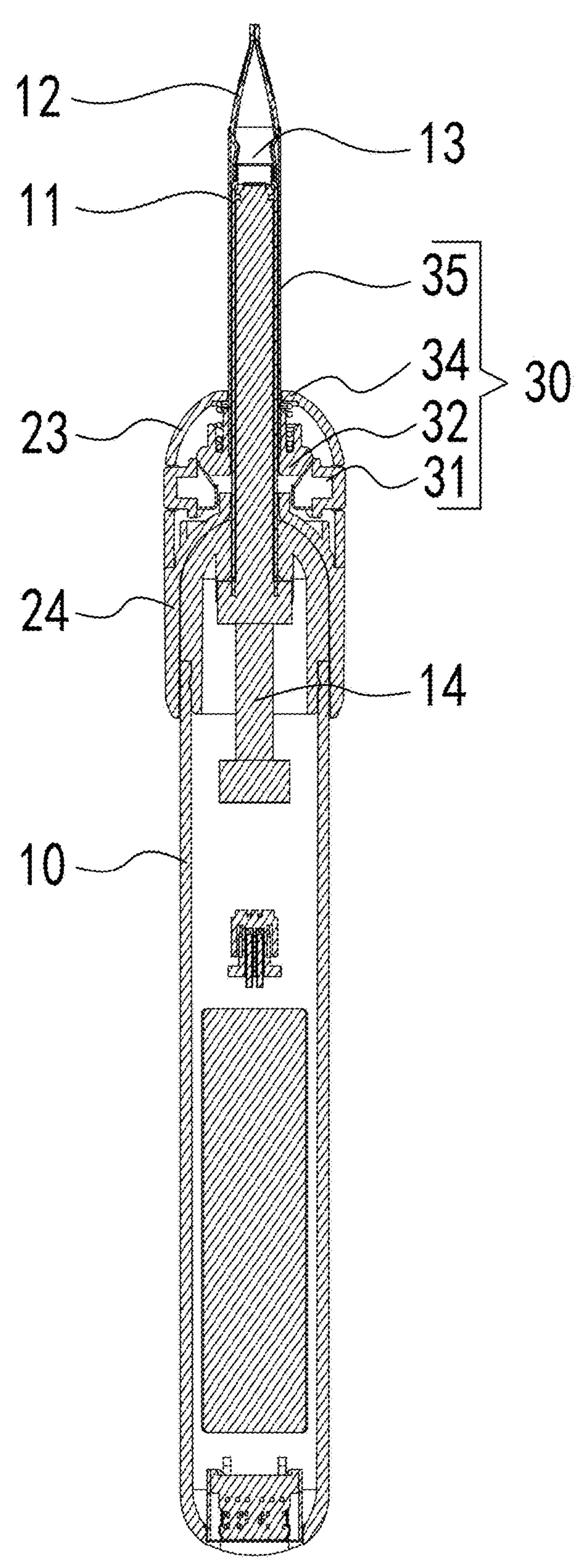
FIG. 3 is a schematic diagram of a cross-sectional structure of visual tweezers according to the present invention in a release state.

Further, as shown in FIGS. 1 to 3, in another embodiment, the tweezer body 10 further includes a camera 13 disposed inside the mounting tube 11 and located near the tweezer head 12, and a control board 14 disposed inside the tweezer body 10. The control board 14 is electrically connected to the camera 13. During operation, the camera 13 captures a clamping area of the tweezer head 12, and the control board 14 transmits an acquired video signal to an external handheld terminal, which enables a user to observe an operation image in real time through the handheld terminal, thereby enhancing the visibility and practicality of the tweezer operation.

The above-mentioned contents are only optional embodiments of the present invention and are not intended to limit the patent scope of the present invention. Under the invention concept of the present invention, the equivalent structural transformations made by using the contents of the specification and the drawings of the present invention, or direct/indirect applications to other related technical fields, are all included in the patent protection scope of the present invention.

The invention claimed is:

1. Visual tweezers, comprising a tweezer body and a driving mechanism; wherein the driving mechanism is configured to be mounted on the visual tweezers to drive a tweezer head on the visual tweezers to clamp or release, comprising:

a mounting base, wherein the mounting base is provided with at least one mounting hole and a driving hole; and a driving assembly, wherein the driving assembly comprises at least one movable key, a driving member, a reset spring, and a driving tube, the at least one movable key is mounted in the at least one mounting hole, the driving member is disposed in the mounting base and movably abuts against the at least one movable key, one end of the reset spring is mounted on the driving member, the other end of the reset spring abuts against an inner wall of the mounting base, one end of the driving tube is located outside the mounting base, and the other end of the driving tube extends into the mounting base from the driving hole and is fixed on the driving member;

wherein the tweezer body comprises a mounting tube and a tweezer head detachably mounted on the mounting tube, the mounting tube is inserted into the driving tube, and two sides of the tweezer head abut against a tube opening of the driving tube.

2. The visual tweezers according to claim 1, wherein the tweezer body further comprises a camera, and the camera is disposed in the mounting tube and arranged near the tweezer head.

3. The visual tweezers according to claim 1 wherein the at least one movable key is provided with an inclined first driving surface, the driving member is provided with a second driving surface cooperating with the first driving surface, and the first driving surface movably abuts against the second driving surface.

4. The visual tweezers according to claim 3, wherein the at least one mounting hole is two mounting holes that are arranged opposite to each other on the mounting base, and the at least one movable key is two movable keys.

5. The visual tweezers according to claim 4, wherein the two movable keys are connected through a connecting member.

6. The visual tweezers according to claim 1, wherein the driving member is provided with a first mounting groove, and the driving tube is inserted into the first mounting groove.

7. The visual tweezers according to claim 1, wherein the driving member is provided with a second mounting groove, and one end of the reset spring is mounted in the second mounting groove.

8. The visual tweezers according to claim 3, wherein the mounting base comprises a first mounting base and a second mounting base, the first mounting base is mounted on the second mounting base to form a mounting space, and the driving member is disposed in the mounting space and movably abuts against the second mounting base.

9. The visual tweezers according to claim 1, wherein the mounting base is provided with a third mounting groove adapted to a visual tweezer body, one end of the visual tweezer body is fixed in the third mounting groove, and a limiting hole corresponding to the driving hole is provided in a groove wall of the third mounting groove.

* * * * *